United States Patent
Ozaki et al.

(10) Patent No.: US 7,531,940 B2
(45) Date of Patent: May 12, 2009

(54) ION INTRODUCER EMPLOYING PIEZOELECTRIC BIMORPH ELEMENT

(75) Inventors: Naotake Ozaki, Yokohama (JP); Tohru Okamoto, Yokohama (JP); Akiko Takahashi, Yokohama (JP)

(73) Assignee: Shiseido Co., Ltd., Chuo-ku, Tokyo (JP)

( * ) Notice: Subject to any disclaimer, the term of this patent is extended or adjusted under 35 U.S.C. 154(b) by 77 days.

(21) Appl. No.: 11/660,749

(22) PCT Filed: Jun. 29, 2005

(86) PCT No.: PCT/JP2005/011986

§ 371 (c)(1),
(2), (4) Date: Aug. 20, 2007

(87) PCT Pub. No.: WO2006/022078

PCT Pub. Date: Mar. 2, 2006

(65) Prior Publication Data

US 2008/0088204 A1    Apr. 17, 2008

(30) Foreign Application Priority Data

Aug. 26, 2004    (JP)    ............................. 2004-246491

(51) Int. Cl.
*H01L 41/113*    (2006.01)
(52) U.S. Cl. .................... 310/319; 310/332; 310/365
(58) Field of Classification Search ............... 310/318, 310/319, 332, 338, 339, 365
See application file for complete search history.

(56) References Cited

U.S. PATENT DOCUMENTS

| 5,667,487 | A | * | 9/1997 | Henley | .................. | 604/20 |
| 2007/0276318 | A1 | * | 11/2007 | Henley | .................. | 604/20 |

FOREIGN PATENT DOCUMENTS

| JP | 57-84059 | 5/1982 |
| JP | 1-120855 | 8/1989 |
| JP | 8-266328 | 10/1996 |
| JP | 11-47281 | 2/1999 |
| JP | 2001-352099 | 12/2001 |
| JP | 3099140 | 10/2003 |
| JP | 2004-87662 | 3/2004 |
| JP | 2004-327408 | * 11/2004 |

* cited by examiner

*Primary Examiner*—Thomas M Dougherty
(74) *Attorney, Agent, or Firm*—Rankin, Hill & Clark LLP

(57) ABSTRACT

A piezoelectric bimorph element two piezoelectric elements to produce an electromotive force by imparting a stress to respective piezoelectric elements. The piezoelectric bimorph element is arranged in an oscillator such that the piezoelectric bimorph element is deformed in the electromotive force generating direction. An electrode having a predetermined area connected with a good electric conductor which is connected to conduct a current generated from the piezoelectric bimorph element is arranged at a patting part interlocked with the oscillator to oscillate. An electrode of opposite pole is connected with the piezoelectric bimorph element through the good electric conductor and arranged at a handle to be coupled with the oscillator, and a rectifier for rectifying an AC electromotive force generated by oscillating the oscillator is arranged to connect the good electric conductors which are connected with both electrodes.

8 Claims, 8 Drawing Sheets

ION INTRODUCER EMPLOYING PIEZOELECTRIC BIMORPH ELEMENT

TECHNICAL FIELD

The present invention relates to an ion introducer for transdermally administering a drug that, as a power source for ion introduction in which a predetermined drug is transdermally administered by means of electrical energy, utilizes an electromotive force resulting from stress deformation of a piezoelectric bimorph element.

BACKGROUND ART

Methods for enhancing permeation of a drug based on supply of a weak electrical current to the skin known as ion introduction or iontophoresis have been disclosed in the conventional art. Several specific examples of these methods will be hereinafter considered.

Ion introduction is based on formation of a closed circuit by, of a positive and negative electrode connected to a power supply, bringing the cathode thereof coated with, for example, a negatively ionized drug into contact at several locations with skin serving as a drug layer through which it is desirable that the drug be permeated and, using a separate location of skin having communication with the skin tissue mentioned above as a receiving layer, bringing the anode into contact with this layer whereupon, utilizing the electrical energy exerted on the drug of the drug layer when a current is conducted from the cathode to the drug layer as a result of a closed circuit being formed, the drug is permeated through the epidermis into the dermis and permeation is enhanced.

The ion introduction described above normally requires that the electrode polarity be kept constant and, accordingly, it uses a direct current power source. In addition, because a drop in drug permeation rate attributable to polarization of the skin caused by the passage of an electrical current is known to occur, there is a need for a voltage to be intermittently applied during the passage of an electrical current in order to prevent this from occurring which necessitates the assembly of a predetermined processor within a circuit designed to do this whereupon, accordingly, there is an inherent problem in this case from the viewpoint of the complexity of the device. In addition, there is an inherent drawback associated with the adoption of configuration that employs a battery as a direct power source from the viewpoint of the need for battery replacement. A typical example of an ion introducer of the type described here is disclosed in Japanese Patent Application No. H7-75882. In addition, while the use of an alternating current power source affords a simple device because it necessitates the assembly of a rectifying element such as a diode alone, there is an inherent drawback associated therewith from the viewpoint of the need for circuit connection with the power source.

On the other hand, as disclosed in Japanese Patent Application Laid-open No. 2004-87662, a so-called piezoelectric bimorph element comprising piezoelectric elements affixed top-to-bottom that generate a piezoelectric current as a result of application of stress, and that is able to produce an electromotive force when stress deformation occurs as a result by stress being imparted to these elements is known.

However, an ion introducer configured to use the electromotive force produced by stress deformation of a piezoelec tric bimorph element as a power source has yet to be devised.

Cited reference 1: Japanese Unexamined Patent Application No. H7-75882

Cited reference 2: Japanese Unexamined Patent Application No. 2004-87662

DISCLOSURE OF THE INVENTION

With the foregoing in view, it is an object of the present invention to provide an ion introducer of a simple and low-cost configuration which, with the electrode polarity kept constant and without need for a complicated circuit, is able to produce an intermittent electromotive force, and which can semi-permanently produce an electromotive force without need for a battery, for battery replacement, or connection to an external power source.

The ion introducer is characterized in that: a piezoelectric bimorph element which has at least two piezoelectric elements and which is configured to produce an electromotive force by a stress imparted to each of the piezoelectric elements is arranged in an oscillator, the piezoelectric bimorph element being arranged to deform in a direction in which the electromotive force is generated: an electrode of a predetermined surface area connected to a good electrical conductor connected to conduct a current generated from the piezoelectric bimorph element is provided in a patting part arranged to interlock and oscillate with the oscillator and, on the other hand, an electrode of reverse pole thereto is connected to the piezoelectric bimorph element by means of a good electrical conductor, this electrode being arranged in a handle coupled to the oscillator; and arrangement of a rectifier for rectifying an alternating electromotive force generated as a result of oscillation of the oscillator to link the good electrical conductors connected to the two electrodes, and is further characterized in that, when the handle coupled to support the oscillator is gripped so as to cause the oscillator to oscillate and, with the oscillator and patting part being oscillated, the electrode provided in the patting part is patted against skin serving as the part to be permeated with the drug, a weak current is conducted to the skin.

The invention is further characterized in that a light-emitting diode is arranged in the wiring of the ion introducer to enable confirmation of whether or not a predetermined current is being conducted during patting, the light-emitting diode emitting light when the predetermined current is being conducted.

The invention is further characterized in that characterized in that in the piezoelectric elements an electromotive force is generated by impact caused by collision of a pressing body, which is fixed to the surface of the piezoelectric elements, against a peripheral member.

The invention is further characterized in that least one of the electrodes is configured from an electrical conductor formed in a needle shape.

And the invention is further characterized in that a moisture-absorbing body impregnated with an ionized drug is laid on an electrode, the moisture-absorbing body being patted on skin.

The effects of the invention are to enable an intermittent electromotive force to be able to be produced without need for a complex circuit and to enable the polarity of the electrodes to be kept constant and, accordingly, to enable an ion introducer of a simple and low-cost structure to be provided.

An additional effect of the invention is to enable the semi-permanent generation of an electromotive force eliminating the need for a battery, for battery replacement, or connection to an external power source.

BEST MODE FOR CARRYING OUT THE INVENTION

Figure 1:
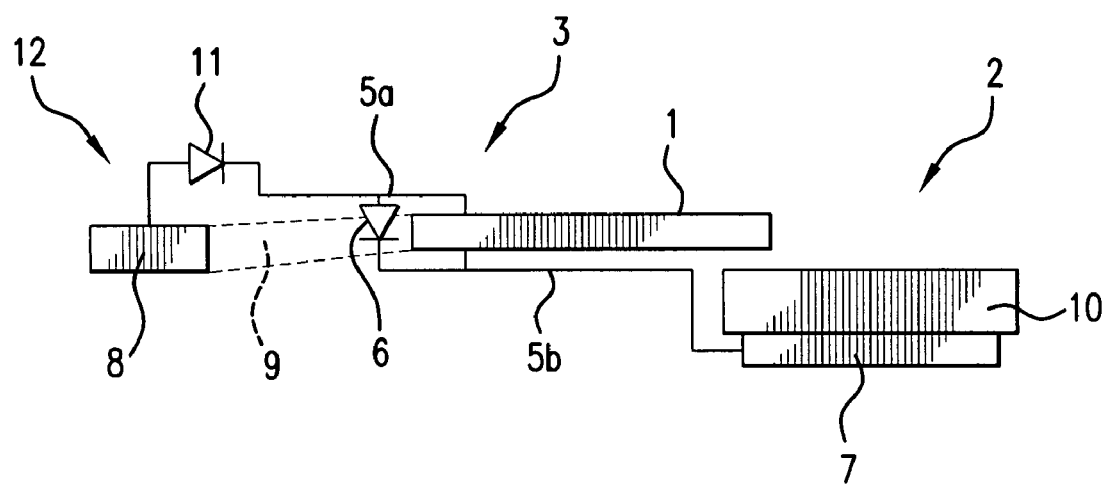
[FIG. 1] is a schematic view showing a main configuration of the present invention.

Preferred embodiments of the present invention will be hereinafter described in detail. FIG. 1 is a schematic view of the main configuration of the present invention, and FIG. 2 is a type diagram showing the stress deformation and electromotive force generation states of a piezoelectric bimorph element (1) of FIG. 1.

As shown in FIG. 1, the main configuration of an ion introducer (2) in which the present invention has application is configured from an oscillator (3) comprising a piezoelectric bimorph element (1), the piezoelectric bimorph element (1) being arranged therein to deform in a direction in which an electromotive force is generated; good electrical conductors (5a) (5b) connected to each of two piezoelectric elements (4a) (4b) from which the piezoelectric bimorph element (1) is formed that serve as an anode and a cathode when the electromotive force caused by stress deformation of the piezoelectric bimorph element (1) is generated; and a rectifier (6) connected to link the good electrical conductors (5a) (5b), an electrode (7) configured from a good conductor of a predetermined surface area being connected to the good electrical conductor (5b) connected to the positive electrode terminal of the rectifier (6) and an electrode (8) configured from a good electrical conductor of a predetermined surface area being connected to the good electrical conductor (5a) connected to the negative electrode terminal of the rectifier (6), the cathode electrode-side electrode (8) of the electrodes (7) (8) being coupled with the oscillator (3) by way of an interlocking body (9) that is interlocked to oscillate with the oscillator (3) and the anode electrode-side electrode (7) being arranged in a handle (10) for supporting the oscillator (3) to enable it to oscillate and, in addition, a light-emitting diode (11) being wired in the good electricity conductor (5a) connected to a negative electrode terminal of the rectifier (6) in alignment with the direction of rectification of the rectifier (6).

Figure 2A:
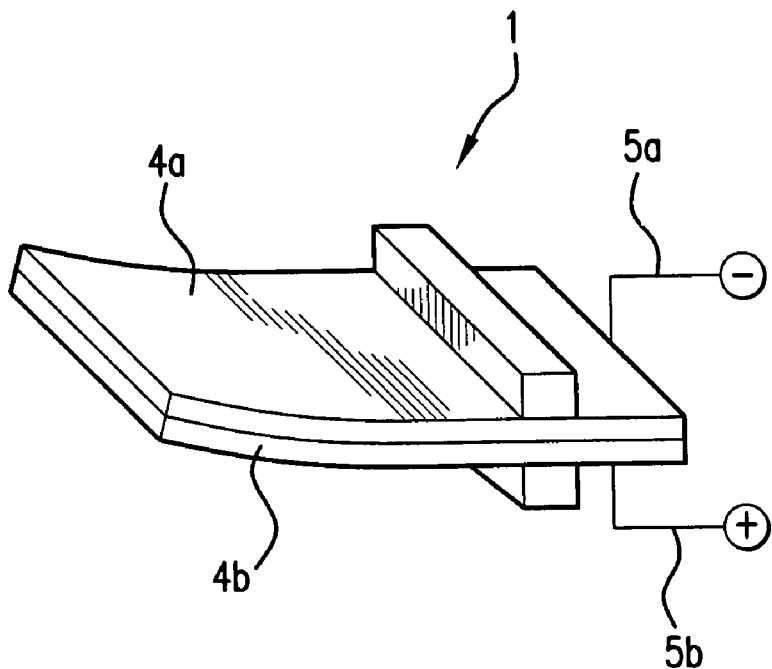
[FIG. 2] is a type diagram showing the stress deformation and electromotive force generation states of the piezoelectric bimorph element shown in FIG. 1.

As shown in FIGS. 2A and B, the piezoelectric bimorph element (1) of this embodiment comprises two piezoelectric elements (4a) (4b), the piezoelectric elements (4a) (4b) being affixed top-to-bottom, and good electrical conductors (5a) (5b) connected to the piezoelectric elements (4a) (4b) respectively, an electromotive force being able to be produced a result of deformation in the top-to-bottom direction caused by stress being imparted to the piezoelectric elements (4a) (4b).

Figure 2B:
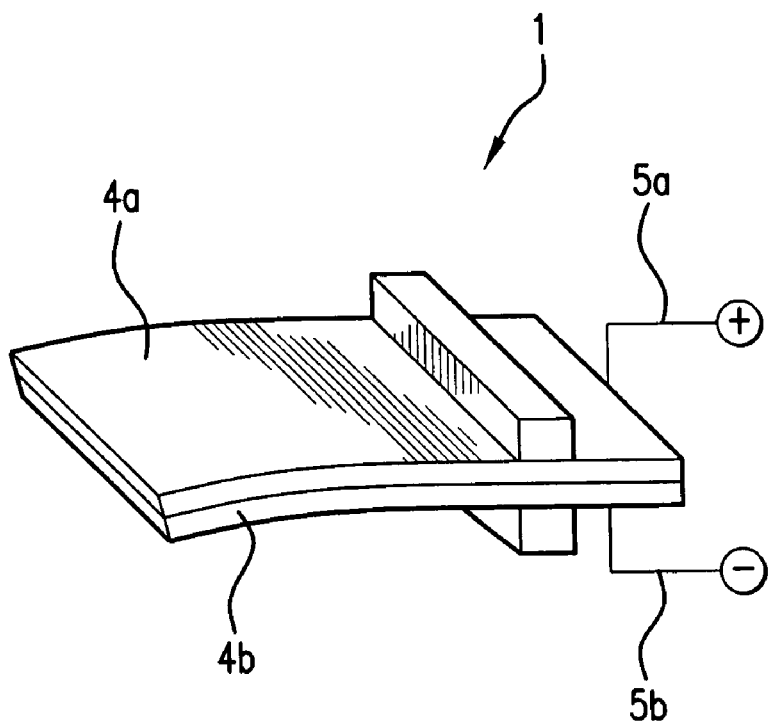

As shown in FIG. 2A, when the piezoelectric bimorph element (1) is inverted upward with the piezoelectric element (4a) contracted and the piezoelectric element (4b) elongated, an electromotive force is generated with the piezoelectric element (4a) serving as a cathode and the piezoelectric element (4b) serving as an anode and, conversely, as shown in FIG. 2B, when the piezoelectric bimorph element (1) is inverted downward with the piezoelectric element (4a) elongated and the piezoelectric element (4b) contracted, an electromotive force is generated with the piezoelectric element (4a) serving as an anode and the piezoelectric element (4b) serving as a cathode. Accordingly, when the piezoelectric bimorph element (1) is caused to oscillate in the top-to-bottom direction, an alternating current in which the direction of each electromotive force is alternated during this reciprocal motion to generate a reverse direction current is established.

However, when an alternating current is conducted to the skin, because of the drop in the rate of permeation of a drug that occurs due to the conducted weak current, there is a need for the polarity of the electrode (8) used to pat the skin to be kept constant and, in order to facilitates this, in this invention the rectifier (6) for performing rectification is arranged within the wiring of the ion introducer (2).

The use of the ion introducer (2) of the configuration described above is based on gripping of the handle (10) in such a way that the skin is abutted against the anode electrode (7) arranged in the handle and, with the handle (10) being shaken up and down or left to right and so on to cause the oscillator (3) and a patting part (12) to oscillate and generate an electromotive force, the electrode (8) arranged in the patting part (12) forming a negative electrode and being patted on the section of skin that constitutes the target area for permeation of the drug whereupon, when this patting is performed, the skin established in series with the ion introducer (2) forms a closed circuit and, on each occasion of the device being patted, a weak current is conducted. The light-emitting diode (11) wired within the ion introducer generates light when the current is being conducted to facilitate verification of current conduction.

EMBODIMENT 1

An embodiment of an ion introducer (13) comprising the main configuration of the ion introducer (2) described in the embodiment outlined above will be hereinafter described with reference to FIGS. 3 to 5. Notably, particulars of this configuration identical to those of FIGS. 1 and 2 have been omitted.

Figure 3:
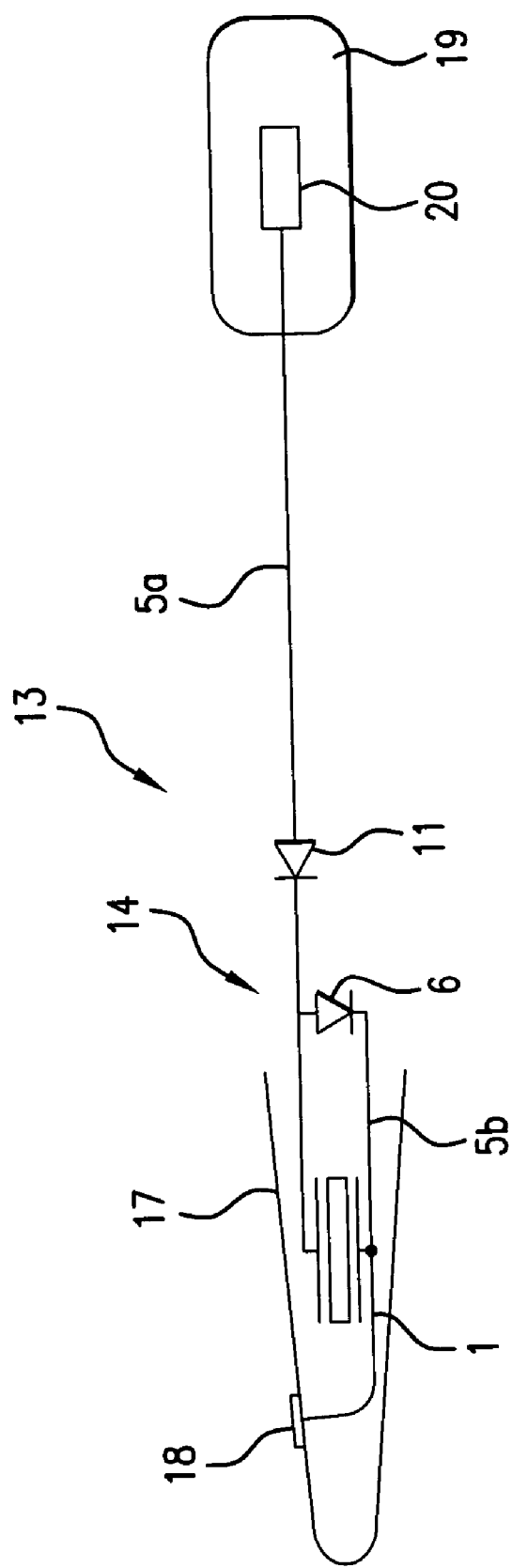
[FIG. 3] is a schematic view of the application of the main configuration of the ion introducer shown in FIG. 1.
Figure 4:
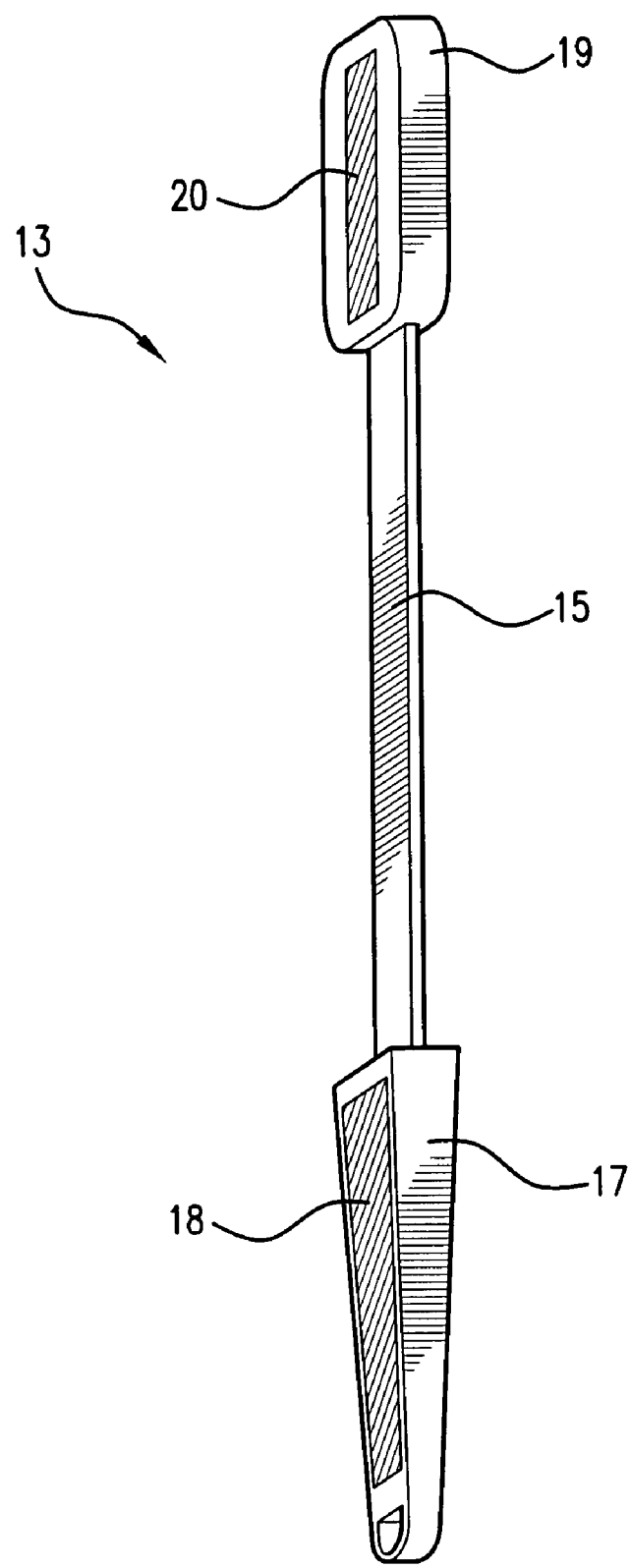
[FIG. 4] is a perspective view of the ion introducer of an embodiment comprising the configuration shown in FIG. 3.
Figure 5:
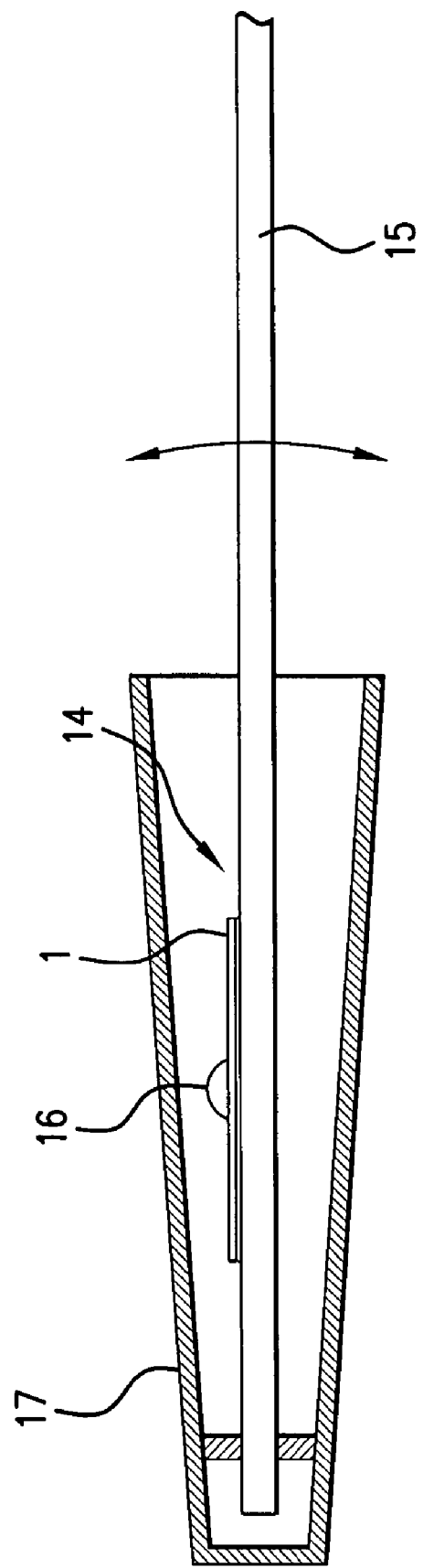
[FIG. 5] is a type diagram showing the oscillated state of an oscillator in which the handle region of the ion introducer of the embodiment is magnified.

FIG. 3 is a schematic view in which the main configuration of the ion introducer (2) shown in FIG. 1 has application, FIG. 4 is a perspective view of the ion introducer (13) of this embodiment comprising the configuration shown in FIG. 3, and FIG. 5 is a type diagram showing the oscillating state of an oscillator (14) in which a handle region of the ion introducer (13) of this embodiment is magnified.

As shown in FIGS. 3 to 5, the ion introducer (13) of this embodiment comprises an oscillator (14) configured from a piezoelectric bimorph element (1) identical to the one described above, a pressing body (16) for pressing the piezoelectric bimorph element (1), a rectifier (6) fixed to the region of the bottom end of an elastic long plate-type oscillating body (15), and an opened hollow handle (17) to which the bottom end of the oscillating body (15) is fixed and which expands in diameter from the bottom end to the top end so as to fully enclose the oscillator (14), the oscillating body (15) being able to oscillate with its bottom end fixed and supported in the inner part of the handle (17). In addition, an anode plate (18) configured from a good electrical conductor with a predetermined surface area and connected to the piezoelectric bimorph element (1) is arranged on the surface of the handle (17). A patting part (19) is fixed to the top end of the oscillating body (15), and a cathode plate (20) configured from a flat good electrical conductor of predetermined surface are and connected to the piezoelectric bimorph element (1) is arranged on the surface of the patting part (19).

The use of the ion introducer (13) of the configuration described above is based on, when the handle (17) is gripped by the hand and shaken up and down, the oscillating body (15) in which the bottom end thereof alone fixed by coupling with the handle (17) being caused to oscillate up and down whereupon, in addition to the stress deformation of the piezoelectric bimorph element (1), because of a further loading of energy on the piezoelectric bimorph element (1) at this time caused by oscillation resulting from collision of the pressing body (16) arranged in the upper part of the piezoelectric bimorph element (1) with the inner side surface of the handle (17), a more reliable electromotive force can be produced.

EMBODIMENT 2

Figure 6:
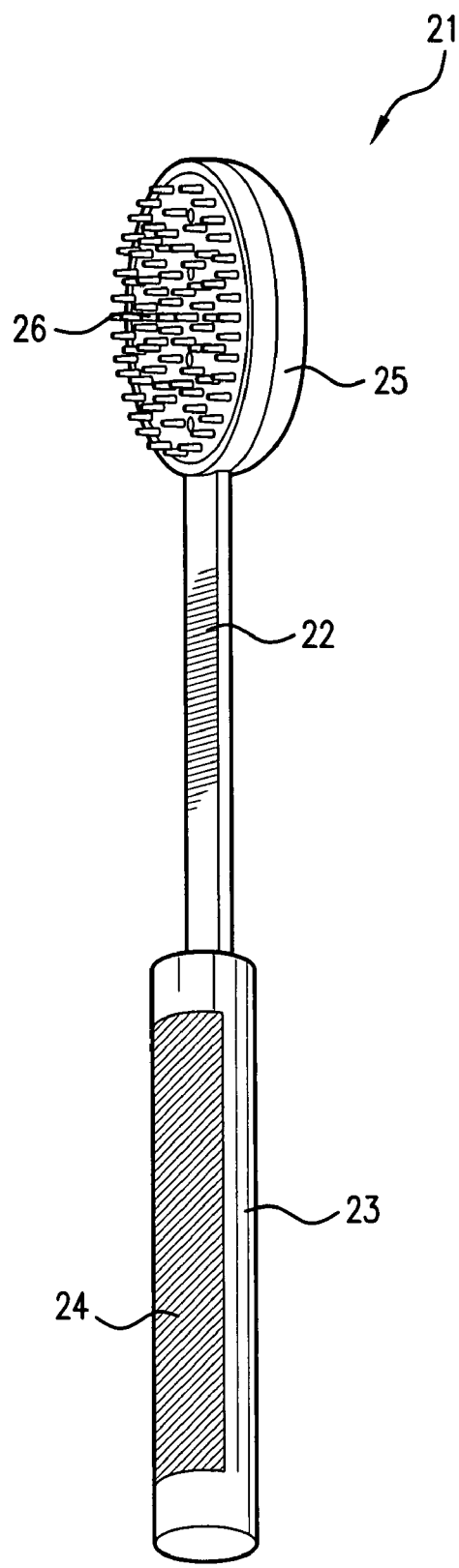
[FIG. 6] is a perspective view showing a modified example of an ion introducer in which the invention has application.

An embodiment of an ion introducer (21) comprising the main configuration of the ion introducer (2) described in the embodiment outlined above will be hereinafter described with reference to FIG. 6. The ion introducer (21) of FIG. 6 is configured to comprise an oscillator (3) configured from a piezoelectric bimorph element (1) and a rectifier (6) provided in the inner part of a hollow, long plate-type oscillating body (22), a cylindrical handle (23) being arranged in the bottom end of the oscillator (3) to support and enable the oscillating body (22) to oscillate, an anode body (24) configured from a good electrical conductor of a predetermined surface area and connected to the piezoelectric bimorph element (1) being arranged on the surface of the handle (23), a patting part (25) being fixed to the top end of the oscillating body (22), and a needle-shape cathode body (26) configured from a good electrical conductor and connected to the piezoelectric bimorph element (1) being arranged on one side surface of the patting part (25).

EMBODIMENT 3

Figure 7:
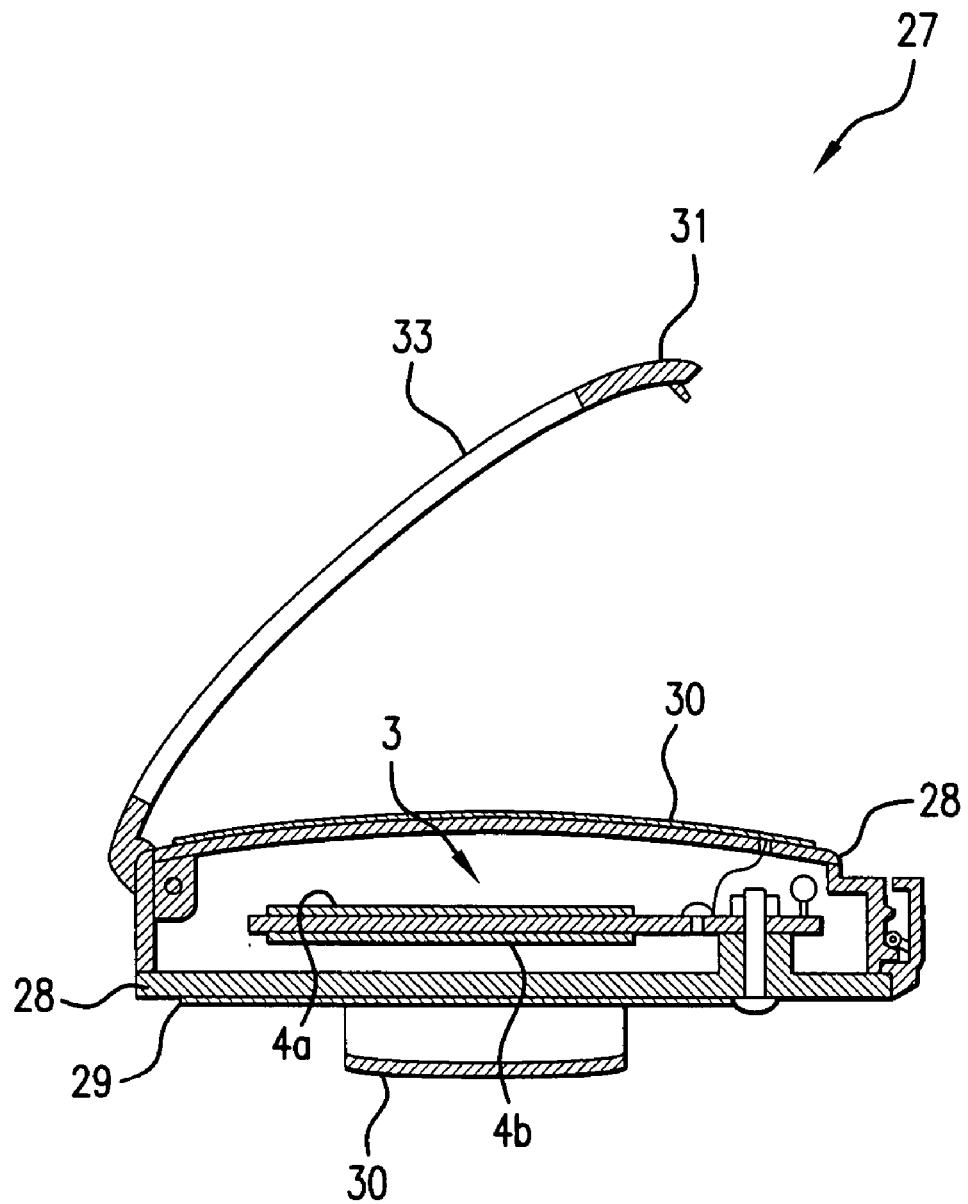
[FIG. 7] is a cross-sectional view of the modified example of the ion introducer in which the invention has application.
Figure 8:
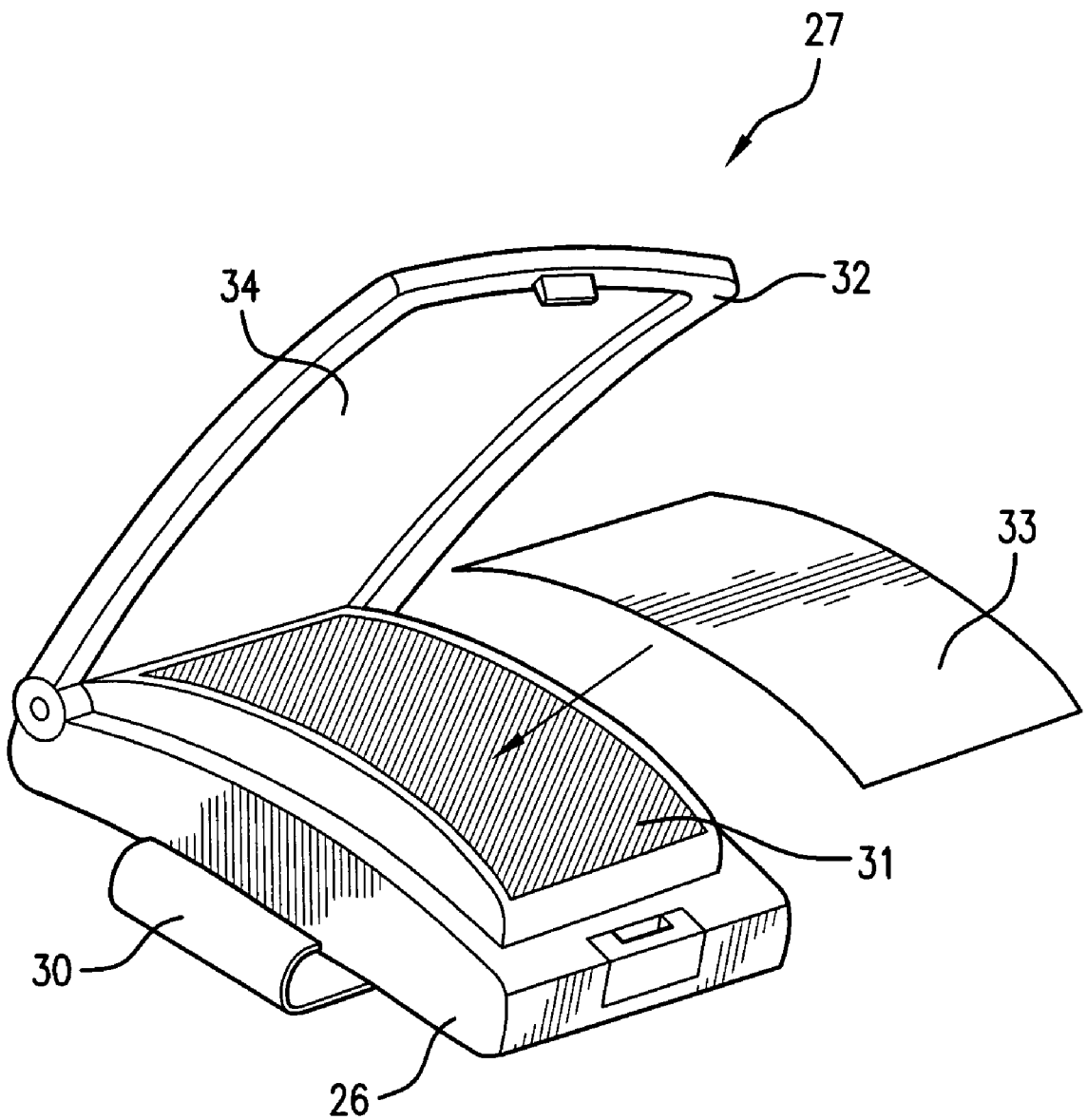
[FIG. 8] is a perspective view showing the mounted state of an absorbent body of the ion introducer shown in FIG. 7.

An embodiment of an ion introducer (27) comprising the main configuration of the ion introducer (2) described in the embodiment outlined above will be hereinafter described with reference to FIGS. 7 and 8. The ion introducer (27) of this embodiment is arranged so that one end of an oscillator (3) comprising a piezoelectric bimorph element (1) and a rectifier (6) is fixed within a box-shaped outer trim body (28) whereupon, when the outer trim body (28) is caused to oscillate in a predetermined direction, the oscillator (3), interlocked with the oscillation thereof, oscillates in the outer trim body (28) and produces an electromotive force. In addition, a flat anode body (29) of a predetermined surface area configured from a good electrical conductor and connected to the piezoelectric bimorph element (1) is arranged in the lower surface of the bottom end of the outer trim body (28). In addition, a mounting stay (30) to facilitate easier support of the ion introducer (27) with the hand is provided in the lower surface of the bottom end of the outer trim body (28).

A planar cathode body (31) of a predetermined surface area configured from a good electrical conductor and connected to the piezoelectric bimorph element (1) is arranged in the upper surface of the top end of the outer trim body (28). In addition, this embodiment is configured to comprise a frame body (32) of surface area and shape substantially the same as the outer trim body (28) of which one end thereof is affixed to the top end of the outer trim body (28) that serves as a fulcrum be able to open and close and of which, with the periphery thereof describing the frame shape, the inner side thereof is open from top to bottom, the exterior shape of the ion introducer (27) being formed to describe the overall shape of a so-called puff.

In the use of the puff ion introducer (27) configured in this way, a paper-type moisture absorbing body (33) of a surface area and shape larger than the surface area and shape of the cathode electrode body (31) and impregnated with, for example, an aqueous solution of a negatively-charged vitamin C derivative formed by dissolving in water is laid on the cathode body (31) of the ion introducer (27) of this embodiment and fixed thereto by closing of the frame body (32). In this state, the paper-type moisture-absorbing body (33) impregnated with the aqueous solution of vitamin C derivative describes an exposed state in which it protrudes slightly upward from an opening part (34) formed in the frame body (32). The use of the puff ion introducer (27) in which the moisture-absorbing body (33) is exposed on the upper surface is based on the puff being patted on the cheeks. Measurement of the vitamin C derivative permeation effect based on testing carried out by the inventors revealed a permeation enhancement effect around twice that possible using a normal puff in which no ion introducer (27) was employed.

The invention claimed is:

1. An ion introducer, characterized in comprising: an oscillator comprising a piezoelectric bimorph element which has at least two piezoelectric elements and which is configured to produce an electromotive force by imparting a stress to each of the piezoelectric elements, the piezoelectric bimorph element being arranged to deform in a direction in which the electromotive force is created: good electrical conductors connected to each of the at least two piezoelectric elements, from which the piezoelectric bimorph element is formed, which serve as an anode and a cathode when the electromotive force produced by stress deformation of the piezoelectric bimorph element is generated; and a rectifier connected to link the good electrical conductors, an electrode configured from a good conductor having a predetermined surface area being connected to the good electrical conductor connected to a positive electrode terminal of the rectifier, and an electrode configured from a good conductor having a predetermined surface area being connected to the good electrical conductor connected to a negative electrode terminal of the rectifier, and at least one of these electrodes being configured to oscillate in synchronization with the oscillator.

2. The ion introducer as claimed in claim 1, characterized in that each of the electrode connected to the good electrical conductor connected to the negative electrode terminal of the rectifier and the electrode connected to the good electrical conductor connected to the positive electrode terminal of the rectifier are fixed to the oscillator.

3. The ion introducer as claimed in claim 1, characterized in comprising a handle coupled with the oscillator, the electrode connected to the good electrical conductor connected to the positive electrode terminal of the rectifier being arranged in the handle.

4. The ion introducer as claimed in claim 1, characterized in comprising a patting part connected to the oscillator,
   the electrode connected to the good electrical conductor connected to the negative electrode terminal of the rectifier being arranged in the patting part.

5. The ion introducer as claimed in claim 1, characterized in that a light-emitting diode is wired to the good electrical conductor connected to the negative electrode terminal of the rectifier in alignment with a direction of rectification of the rectifier.

6. The ion introducer as claimed in claim 1, characterized in being configured to generate in the piezoelectric elements an electromotive force of impact caused by collision of a pressing body, which is fixed to the surface of the piezoelectric elements, against a peripheral member.

7. The ion introducer as claimed in claim 1, characterized in that at least one of the electrodes is configured from an electrical conductor formed in a needle shape.

8. The ion introducer as claimed claim 1, characterized in being configured to lay a moisture-absorbing body impregnated with an ionized drug on the electrodes, and pat skin with the moisture-absorbing body.

* * * * *